United States Patent
Park et al.

(10) Patent No.: US 10,551,050 B1
(45) Date of Patent: Feb. 4, 2020

(54) VIRTUAL AUGMENTED REALITY PROVIDING METHOD AND VIRTUAL AUGMENTED REALITY PROVIDING APPARATUS AND SCENT PROJECTOR USING THE METHOD

(71) Applicant: Electronics and Telecommunications Research Institute, Daejeon (KR)

(72) Inventors: Jun Seok Park, Daejeon (KR); Joon Hak Bang, Daejeon (KR); Hae Ryong Lee, Daejeon (KR); Sung June Chang, Daejeon (KR); Jong Woo Choi, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 16/288,445

(22) Filed: Feb. 28, 2019

(30) Foreign Application Priority Data

Dec. 19, 2018 (KR) .......... 10-2018-0165034

(51) Int. Cl.
*F21V 33/00* (2006.01)
*G06T 19/00* (2011.01)
*A61L 9/03* (2006.01)
*F21Y 115/10* (2016.01)

(52) U.S. Cl.
CPC ............... *F21V 33/00* (2013.01); *A61L 9/03* (2013.01); *G06T 19/006* (2013.01); *F21Y 2115/10* (2016.08)

(58) Field of Classification Search
CPC .......... F21V 33/00; A61L 9/03; G06T 19/006; F21Y 2115/10
See application file for complete search history.

(56) References Cited

U.S. PATENT DOCUMENTS

| | | |
|---|---|---|
| 10,065,113 B1 | 9/2018 | Mostovoy |
| 2012/0050325 A1 | 3/2012 | Joo et al. |
| 2013/0191250 A1 | 7/2013 | Bradley et al. |
| 2017/0177085 A1 | 6/2017 | Sun et al. |
| 2017/0273828 A1* | 9/2017 | Fateh ............... A61F 9/0026 |
| 2018/0120277 A1 | 5/2018 | Chang et al. |
| 2018/0280556 A1 | 10/2018 | Fateh |

FOREIGN PATENT DOCUMENTS

WO 2016164917 A1 10/2016

* cited by examiner

*Primary Examiner* — Andrew L Sniezek
(74) *Attorney, Agent, or Firm* — William Park & Associates Ltd.

(57) ABSTRACT

Provided are an apparatus and method for providing a virtual augmented reality using a scent projector, the method including: analyzing an input virtual augmented reality media related sound to extract an amplitude and a frequency of the sound at a predetermined interval of time; converting the amplitude of the sound into an odor concentration signal; converting the frequency of the sound into an odor quality signal; and controlling the scent projector to emit a scent in response to the odor concentration signal and the odor quality signal.

17 Claims, 7 Drawing Sheets

VIRTUAL AUGMENTED REALITY PROVIDING METHOD AND VIRTUAL AUGMENTED REALITY PROVIDING APPARATUS AND SCENT PROJECTOR USING THE METHOD

CLAIM FOR PRIORITY

This application claims priority to Korean Patent Application No. 2018-0165034 filed on Dec. 19, 2018 in the Korean Intellectual Property Office (KIPO), the entire contents of which are hereby incorporated by reference.

BACKGROUND

1. Technical Field

Example embodiments of the present invention relate to a virtual augmented reality providing method and a virtual augmented reality providing apparatus and scent projector using the same, and more specifically, to a method of providing a multi-modal fused virtual augmented reality and a virtual augmented reality providing apparatus and scent projector using the same

2. Related Art

Virtual reality (VR) is a technology that provides a virtual experience like a real space by providing a virtual space environment giving a sensation of reality utilizing an actual picture of a real world or graphic technology. The VR technology is characterized in having enhanced true presence and immersion by generating a virtual space similar to a real space through images and sounds output in a range of 360 degrees and by interacting with a. situation existing in a virtual reality using an external device.

A representative virtual reality apparatus is a head-up display (e.g., a head-mounted display (HMD)) formed in a helmet shape worn on the head and includes commercial products such as a VR headset made by Samsung Electronics Co, Rift made by Oculus VR, HTC Vibe made by HTC, and PlayStation VR made by Sony. Augmented reality (AR) may combine virtual information with an image of a. real space in real time to provide an environment in which a user interacts with the virtual information, and a representative AR product has the form of glasses with commercial products including Vuzix's 'Vuzix M100' and Google's Google Glasses, and the like.

A virtual augmented reality (a mixed reality), in which virtual and augmented realities are fused, has a representative product, Microsoft HoloLens. As such, various apparatuses for virtual realities and augmented realities are being developed and mostly take the form of goggles worn on the face while serving to provide enhanced audio and video effects, such as three-dimensional (3D) video stream and surround stereo sound, on the basis of high-performance displays, head positioning and tracking, space scanning, and recognition technologies.

As such, the conventional technologies for experiencing five senses in virtual and augmented realities generally feature a system that provides a stimulus for a sensory experience in a virtual reality by providing a plurality of sensory stimuli, such as an odor, vibration, cold/hot air, water spray, and the like, through a mask attached to a 3D goggle of a virtual reality system.

Such a conventional method has limitations that an odor is output according to a natural flow of air, and, in executing various sensory stimuli, a sensory stimulation event marker needs to be inserted into content in advance, in addition, the conventional portable virtual and augmented reality apparatuses exert an influence only on the senses of sight and hearing, that is, major senses of a human.

SUMMARY

Accordingly, example embodiments of the present invention are provided to substantially obviate one or more problems due to limitations and disadvantages of the related art.

Accordingly, embodiments of the present disclosure provide an apparatus for providing a virtual augmented reality using a scent projector.

Accordingly, embodiments of the present disclosure provide a scent projector for providing a virtual augmented reality.

Accordingly, embodiments of the present disclosure provide a method of providing a virtual augmented reality using a scent projector.

In order to achieve an objective of the present disclosure, an apparatus for providing a. virtual augmented reality using a scent projector may comprise a processor; and a memory that stores at least one command to be executed by the processor, wherein the at least one command includes: a command that analyzes an input virtual augmented reality media related sound to extract an amplitude and a frequency of the sound at a predetermined interval of time; a command that converts the amplitude of the sound into an odor concentration signal; a command that converts the frequency of the sound into an odor quality signal; and a command that controls the scent projector to emit a scent in response to the odor concentration signal and the odor quality signal.

The command that converts the amplitude of the sound into the odor concentration signal may include a command that divides a full amplitude range of the sound into a plurality of sections; and a command that sets a concentration of odor for each of the divided sections respectively.

The command that sets the concentration of odor for each of the divided sections respectively may include a command that sets a low concentration of the odor to a section having a small amplitude among the plurality of sections and sets a high concentration of the odor to a section having a large amplitude among the plurality of sections.

The command that converts the frequency of the sound into the odor quality signal may include a command that divides an audible frequency range in a frequency range of the sound into a plurality of sections; and a command that maps a quality of odor to each of the divided sections respectively.

The command that maps the quality of the odor to each of the divided sections respectively may include a command that maps a heavy or deep scent to a section including a low frequency band and maps a sweet or aromatic acid scent to a section including a high frequency band.

The scent projector may include a scent storage including a plurality of scent storage modules, each of which stores a corresponding scent; a light emitting diode (LED) lamp configured to heat the scent stored in the scent storage to expedite vaporization of the scent; an air pump configured to suction external air and store the suctioned air in an air tank; a plurality of input valves connected to the air tank and individual scent storage modules; and an output valve connected to the individual scent storage modules to guide scent molecules output from the individual scent storage modules to a corresponding jetting nozzle.

The scent projector may further include a plurality of jetting nozzles, each set to have a separate inclination angle depending on a position, wherein the scent molecules jetted from the plurality of jetting nozzles are directed to a same position in a space.

The at least one command may further include a command that receives a scent emission control signal from a user terminal, selects a module in the scent projector corresponding to the control signal, and controls the module in the scent projector in response to the received scent emission control signal.

In order to achieve another objective of the present disclosure, a scent projector for providing a virtual augmented reality may comprise a scent storage including a plurality of scent storage modules in which individual scents are stored; a light emitting diode (LED) lamp configured to heat the scent stored in the scent storage to expedite vaporization of the scent; an air pump configured to suction external air and store the suctioned air in an air tank; a plurality of input valves connected to the air tank and individual scent storage modules; an output valve connected to the individual scent storage module to guide scent molecules output from the individual scent storage modules to a corresponding jetting nozzle; and a processor configured to analyze an input virtual augmented reality media related sound to extract an amplitude and a frequency of the sound at a predetermined interval of time, convert the amplitude of the sound into an odor concentration signal, convert the frequency of the sound into an odor quality signal, and control at least one of the scent storage, the LED lamp, to the air pump, the input valve, and the output valve to emit a scent in response to the odor concentration signal and the odor quality signal.

The scent projector may further comprise a plurality of image input devices configured to obtain at least one of an image related to a scene of a reality space and depth related data of an object in the reality space; a display unit configured to display at least one of an image and a virtual object that are input from the image input device; and a speaker configured to output sound in synchronization with an output multimedia content under control of the processor.

The scent projector may further comprise a plurality of jetting nozzles, each set to have a separate inclination angle depending on a position, wherein the scent molecules jetted from the plurality of jetting nozzles are directed to a same position in a space.

In order to achieve a further objective of the present disclosure, a method of providing a virtual augmented reality using a scent projector may comprise analyzing an input virtual augmented reality media related sound to extract an amplitude and a frequency of the sound at a predetermined interval of time; converting the amplitude of the sound into an odor concentration signal; converting the frequency of the sound into an odor quality signal; and controlling the scent projector to emit a scent in response to the odor concentration signal and the odor quality signal.

The converting of the amplitude of the sound into the odor concentration signal may include dividing a full amplitude range of the sound into a plurality of sections; and setting a concentration of odor for each of the divided sections respectively.

The setting of the concentration of the odor for each of the divided sections respectively may include setting a low concentration of the odor to a section having a small amplitude among the plurality of sections; and setting a high concentration of the odor to a section having a large amplitude among the plurality of sections.

The converting of the frequency of the sound into the odor quality signal may include dividing an audible frequency range in a frequency range of the sound into a plurality of sections; and mapping a quality of odor to each of the divided sections respectively.

The mapping of the quality of the odor to each of the divided sections respectively may include mapping a heavy or deep scent to a section including a low frequency hand; and mapping a sweet or aromatic acid scent to a section including a high frequency band.

The method may further comprise receiving a scent emission control signal from the user terminal; selecting a module in the scent projector corresponding to the scent emission control signal; and controlling the module in the scent projector in response to the received scent emission control signal.

The module in the scent projector includes at least one of a scent storage, an input valve, an output valve, an air pump, an air tank, a light emitting diode (LED) lamp, and a pressure sensor.

The method may further comprise determining a scent corresponding to an input user interaction; and controlling the scent projector to emit the determined scent.

The user interaction includes at least one of a gaze of a user and a motion of a user that are related to an odor-associated virtual space or object in the virtual space.

BRIEF DESCRIPTION OF DRAWINGS

Example embodiments of the present invention will become more apparent by describing example embodiments of the present invention in detail with reference to the accompanying drawings, in which.

DESCRIPTION OF EXAMPLE EMBODIMENTS

Example embodiments of the present invention are disclosed herein. However, specific structural and functional details disclosed herein are merely representative for purposes of describing example embodiments of the present invention, and example embodiments of the present invention may be embodied in many alternate forms and should not be construed as limited to example embodiments of the present invention set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention. Like numbers refer to like elements throughout the description of the figures.

It will be understood that, although the terms first, second, etc. may be used herein describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between", "adjacent" versus "directly adjacent", etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should also be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Hereinafter, exemplary embodiments of the present invention will be described in detail with reference to the accompanying drawings.

The present invention relates to an invention concerning a virtual augmented reality headset apparatus incorporated with a scent projector capable of providing a stimulus of smell together with sight and hearing to generate a true presence and a sense of immersion for a user in a virtual augmented reality environment and a manipulation thereof and is directed to virtual reality and augmented reality system technologies.

The present invention proposes a method of providing a new user experience that is not provided by the existing virtual augmented reality apparatus by providing a method of generating an odor in the existing audio/video based virtual and augmented realities, controlling the intensity and quality of the odor using a sound, and allowing an olfactory display to be experienced on the basis of a user's motion.

The present invention proposes a virtual augmented reality apparatus for providing multi-modalities, in which the senses of sight (an image), hearing (a sound), and smell (an odor) are fused, and a manipulation method for providing an experience of a true presence and a sense of immersion in a virtual augmented reality space on the basis of the virtual augmented reality apparatus. To this end, the present invention provides a multi-modal fused virtual augmented reality providing apparatus, a headset shaped-scent projector belonging thereto, and a method of generating an odor output control signal of the scent projector using a sound signal and emitting scent on the basis of a user's motion, thereby expanding an audio-vision based user experience provided by the existing virtual and augmented realties to provide an interactive vision, hearing, and smell sensibility virtual augmented reality platform.

Hereinafter, example embodiments according to the present invention will he described in detail with reference to the accompanying drawings.

Figure 1:
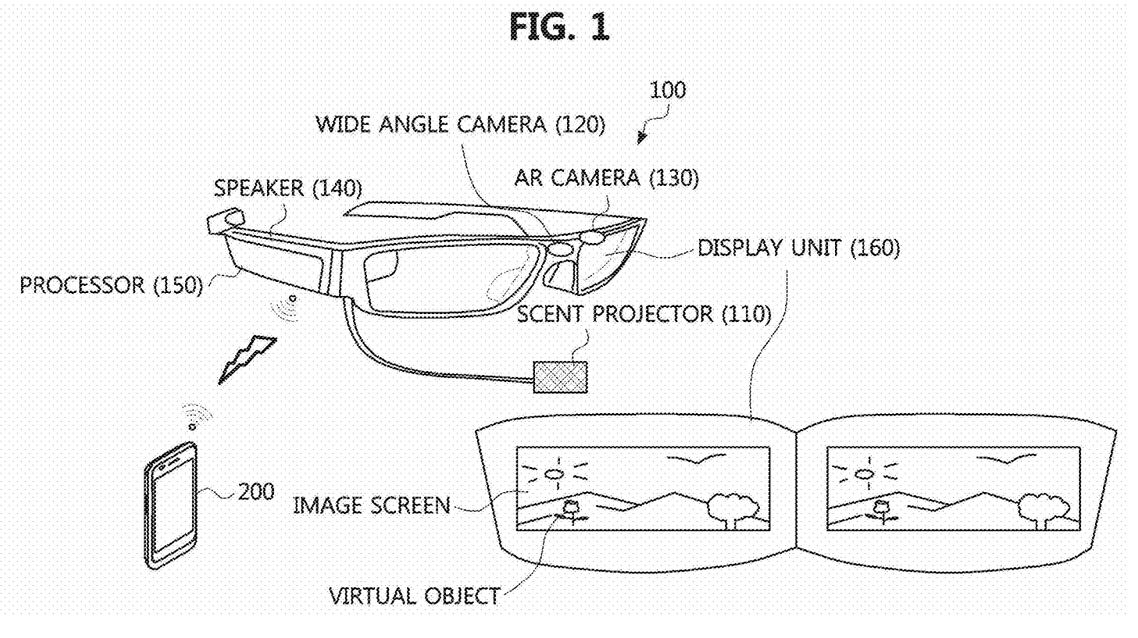
FIG. 1 is a conceptual diagram illustrating a virtual augmented reality apparatus according to an example embodiment of the present invention.

FIG. 1 is a conceptual diagram illustrating a virtual augmented reality apparatus according to an example embodiment of the present invention.

A virtual augmented reality providing apparatus according to the example embodiment of the present invention is a multi-modal apparatus for outputting an odor, a sound, and an image and transmitting the output odor, sound, and image to a user.

Referring to FIG. 1, the virtual augmented reality providing apparatus according to the example embodiment of the present invention may include a wearable user device 100 and a user terminal 200.

The virtual augmented reality providing apparatus according to the example embodiment of the present invention may include only the wearable user device and may exist in the form of modules inside the wearable user device.

The wearable user device 100 may be a glasses-shaped device, a headset, a head mount display (HMD), a head up display (HUD), or the like. In addition, the user terminal 200 may be a notebook computer, a personal digital assistant (PDA), a portable multimedia player (PMP), a PlayStation Portable (PSP), a wireless communication terminal, a smart phone, a smart watch, or the like.

A user may perform control on the virtual augmented reality providing apparatus or the wearable user device 100 through a user interface provided by the user terminal 200.

In detail, the wearable user device 100 includes a scent projector 110, a first image input device 120, a second image input device 130, a speaker 140, a processor 150, and a to display unit 160.

The scent projector 110 stores various types of scents and emits a corresponding scent in response to a control signal. A detailed structure of the scent projector 110 will be described in detail with reference to FIG. 2 below.

The first image input device 120 may be a wide-angle camera for acquiring a scene of a real space, that is, a general camera, including a plurality of camera modules.

The second image input device 130 may be an augmented reality (AR) camera (i.e., a depth camera) that measures the depth of a subject in a real space by radiating light to the subject and measuring the time of return of the light reflected from the subject in order to calculate the distance between a camera lens and the subject.

The speaker 140 outputs a corresponding sound in synchronization with a multimedia content output from the virtual augmented reality apparatus under the control of the processor 150.

The processor 150 drives the scent projector 110 in response to a control signal received from the user terminal 200 through wireless communication. The processor 150 may perform preprocessing on input and output of the speaker 140. In addition, the processor 150 may serve to identify and segment an object associated with an odor from images input from the first image input device 120 and the second image input device 130 and convert the input images into a virtual augmented reality related three-dimensional (3D) image.

Meanwhile, an operation of identifying an odor-related object and converting input images into a 3D image may be performed by the user terminal 200. In this case, a result of the operation may be transmitted to the wearable user device 100 and may be displayed through the display unit 160.

The display unit 160 does not only output an image input from the camera but also allows a virtual object processed by the processor 150 or the user terminal 200 to overlap an image input from the camera and then be displayed.

Although not shown in FIG. 1, the wearable user device 100 may further include a wireless communication module, and the wireless communication module may communicate with the user terminal 200 through wireless communication and, in particular, a near-field wireless communication method.

As described through the example embodiment shown in FIG. 1, the virtual augmented reality providing apparatus according to the present invention may be implemented in various forms such as a wearable user device, a module in a wearable user device, and a concept including a wearable user device and a user terminal.

In summary, the virtual augmented reality providing apparatus according to the present invention is an apparatus for providing a virtual augmented reality using a scent projector and includes a processor and a memory for storing at least one command to be executed by the processor.

The at least one command may include: a command for analyzing an input virtual augmented reality media related sound to extract an amplitude and a frequency of the sound at a predetermined interval of time; a command for converting the amplitude of the sound into an odor concentration signal; a command for converting the frequency of the sound into an odor quality signal; and a command for controlling the scent projector to emit a scent in response to the odor concentration signal and the odor quality signal.

Figure 2:
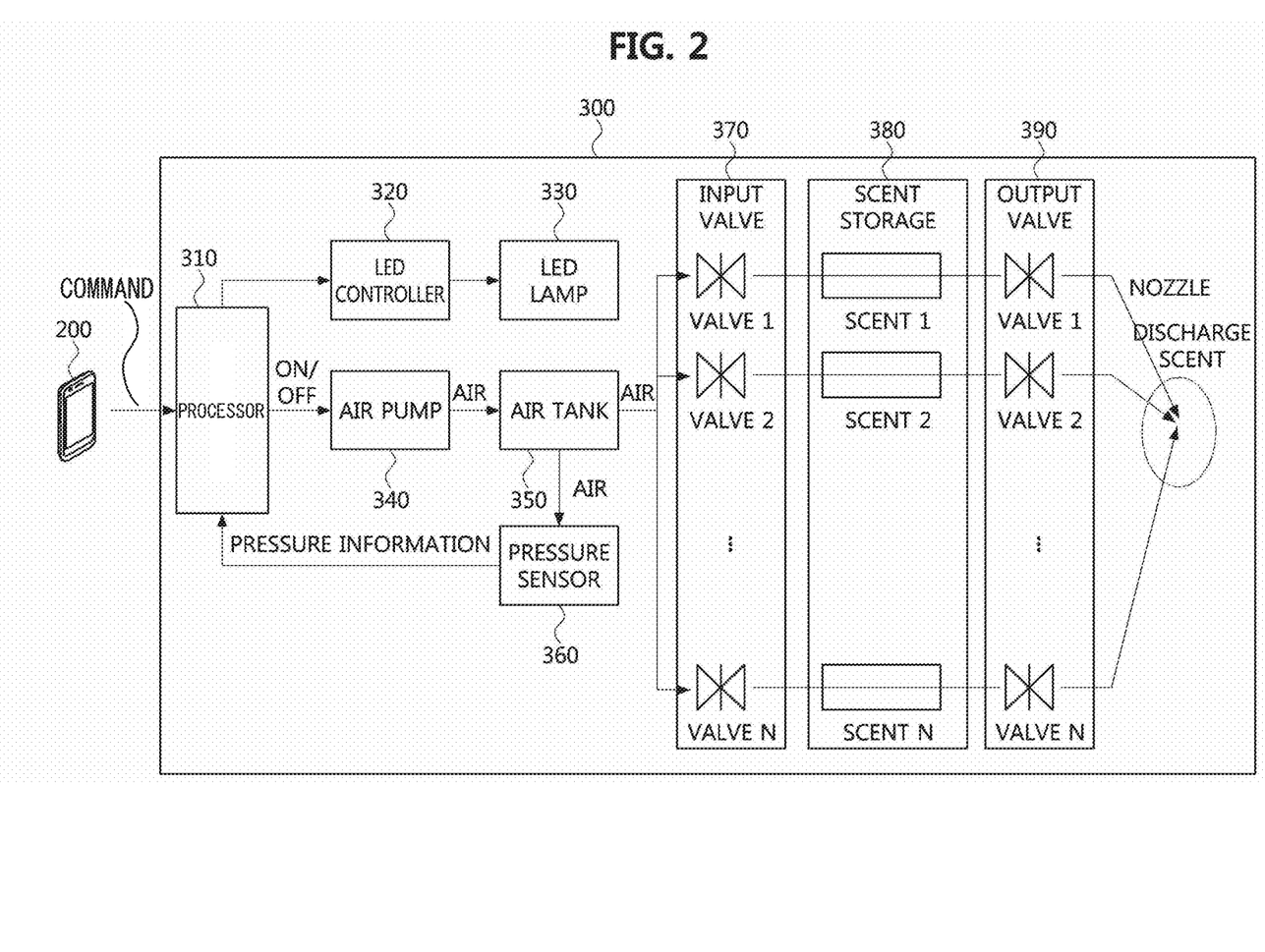
FIG. 2 is a block diagram illustrating a scent projector according to an example embodiment of the present invention.

FIG. 2 is a block diagram illustrating a scent projector 300 according to an example embodiment of the present invention.

The scent projector 300 according to the example embodiment of the present invention serves to output an odor and transmit the output odor to a user. As described above with reference to FIG. 1, the scent projector 300 may be attached to or mounted on the wearable user device.

The scent projector 300 according to the example embodiment shown in FIG. 2. to includes a processor 310, a light emitting diode (LED) controller 320, an LED lamp 330, an air pump 340, an air tank 350, a pressure sensor 360, an input valve 370, a scent storage 380, and an output valve 390.

According to the example embodiment, the processor 310 may perform the same function as that performed by the processor 150 shown in FIG. 1 or may serve to control only the scent projector 300 rather than an overall operation of the wearable user device.

First, the scent storage 380 stores various types of scents to form a scent palette. Here, as shown in FIG. 2, the scent storage 380 includes a plurality of individual storage modules each storing an individual scent, and each storage module is connected to an input valve and an output valve for a storage module corresponding thereto.

Here, the plurality of scents may include various types of scents that represent various fragrance notes, such as citrus, vanilla, almond, herb, spice, wood flavor, and the like, that is, impression representations.

The LED lamp 330 heats a solid scent stored in the scent storage 380 to expedite vaporization of the solid scent and displays an operating state. The input valve 370 and the output valve 390 serve as switches for discharging odorants distributed in a head space of the scent storage 380 to the outside using the pressure of air stored in the air tank 350. The air pump 340 suctions external air and compresses the air to be stored in the air tank 350, and the pressure sensor 360 checks the pressure value of the air tank 350.

The processor 310 may control the modules in the scent projector 300, particularly, the LED controller 320, the air pump 340, the pressure sensor 360, and the input and output valves 370 and 390. To this end, the scent projector 300 may include a memory for storing at least one command to be executed by the processor 310 and a result of the command execution.

Here, the at least one command may include: a command that allows the processor 310 to analyze an input virtual augmented reality media related sound to extract an amplitude and a frequency of the sound at a predetermined interval of time; a command that allows the processor 310 to convert the amplitude of the sound into an odor concentration signal; a command that allows the processor 310 to convert the frequency of the sound into an odor quality signal; and a command that allows the processor 310 to control the scent projector 300 to emit a scent in response to the odor concentration signal and the odor quality signal.

Here, the command for converting the amplitude of the sound into an odor concentration signal may include: a command for dividing a full amplitude range of the sound into a plurality of sections; and a command for setting a different concentration of odor for each of the divided sections.

The command for setting a different concentration of odor for each of the divided sections may include a command that sets a low concentration of the odor to a section having a small amplitude among the plurality of sections and sets a high concentration of the odor to a section having a large amplitude among the plurality of sections.

The at least one command may further include a command that receives a scent emission control signal from the user terminal 200 selects a module in the scent projector 300 corresponding to the scent emission control signal, and controls the module in the scent projector 300 in response to the received scent emission control signal.

The scent projector 300 according to the example embodiment of the present invention may operate in a procedure described below.

The processor 310 always or periodically checks an air pressure of the air tank 350 through the pressure sensor 360. When the air pressure of the air tank 350 drops at a certain level or lower, the processor 310 operates the air pump 340 to inject air into the air tank 350 so that the air pressure in the air tank 350 is kept at a constant Meanwhile, the user terminal 200, which may be implemented by a smart phone or a smart watch, transmits, to the scent projector 300, a control command for controlling the scent projector 300 according to a user command.

The processor 310 of the scent projector 300, upon receiving the control command from the user terminal 200, checks the validity of the command and controls a valve corresponding to the command. Here, the control command includes commands such as a 'read an air pressure' command, a 'pressurize' command, an 'emit a scent' command, a 'control an LED Pulse Width Modulation (PWM)' command, a 'stop' command, and the like.

For example, when receiving the 'pressurize' command from the user terminal 200, the processor 310 opens an input valve 370 connected to a module corresponding to the command among the various scent modules included in the scent storage 380 such that the module is filled at a set pump speed to achieve an output pressure of 0 kPa to 44 kPa.

In addition, for example, when receiving the 'control an LED PWM' command, the processor 310 may adjust the LED brightness to a predetermined value such that the scent storage 380 is heated without a separate heater, assisting in vaporization of a scent.

Additionally, when receiving the 'emit a scent' command, the processor 310 opens an output valve connected to a selected scent module for a set period of time to jet scent molecules together with the air. The jetting of scent molecules is achieved such that scent molecules are always jetted to a constant position irrespective of an output valve with an inclined structure of nozzles according to the example embodiment of the present invention.

When receiving the 'read an air pressure' command from the user terminal 200, the processor 310 reads a current pressure value of the air tank 350 to check the current pressure state of the air tank 350.

Figure 3:
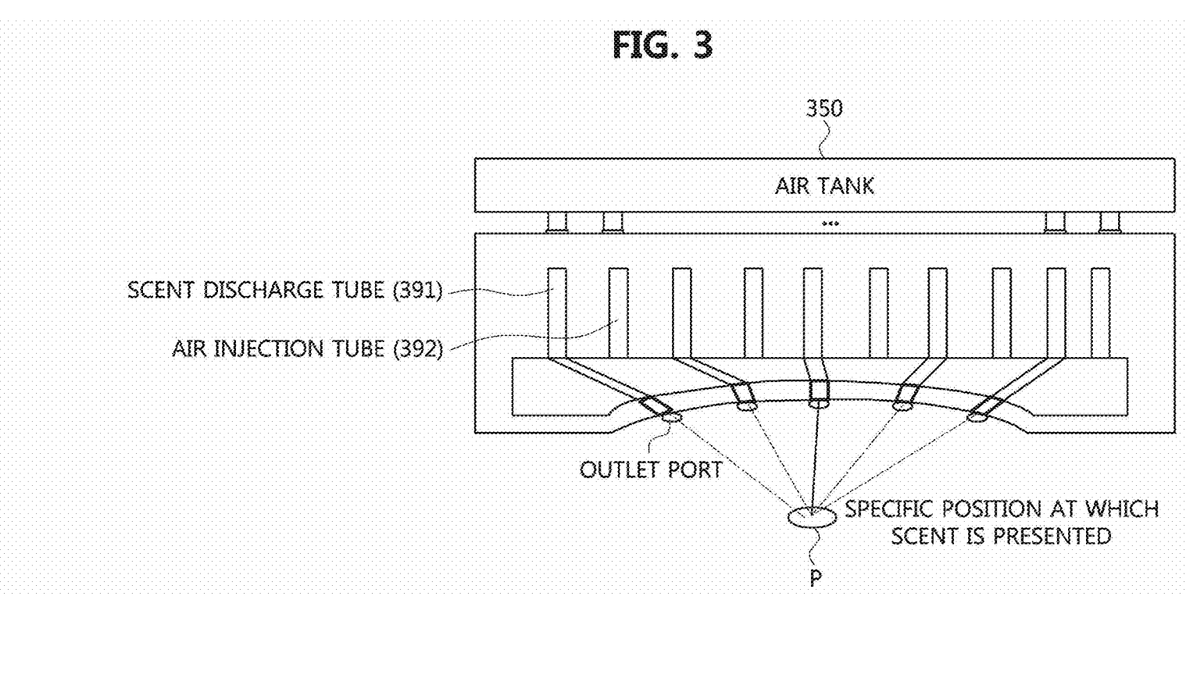
FIG. 3 is a view illustrating a scent discharge nozzle structure of a scent projector to according to an example embodiment of the present invention.

FIG. 3 is a view illustrating a scent discharge nozzle structure of the scent projector according to an example embodiment of the present invention.

FIG. 3 illustrates a detailed structure of a scent outlet when a scent is output from an output valve of the scent projector 300.

Referring to FIG. 3. the scent outlet according to the example embodiment of the present invention connected to the air tank 350 includes scent discharge tubes 391 connected to the individual scent modules and additionally includes air injection tubes 392 corresponding to the respective scent discharge tubes 391. Accordingly, scent molecules jetted through the scent discharge tube 391 of the scent outlet are mixed with air jetted through the air injection tube 392 and discharged through an outlet port.

In this case, discharge nozzles for finally discharging the scent molecules may each be set to have a separate inclination angle. That is, the inclination angle of the discharge nozzle may be set differently according to a relative position in which the discharge nozzle is arranged in the scent outlet, preferably, such that a plurality of the discharge nozzles discharge air molecules to the same spatial position (a point P in FIG. 3).

Meanwhile, a multimodal virtual augmented reality apparatus according to another example embodiment of the present invention may fuse a sound, an image, and an odor and express a result of the fusion. The present invention generates an odor output control signal according to the frequency and amplitude of a sound by maximizing the influence by a cross-modal effect of a sound and an odor to increase the sensibility of the user. The present invention also controls the intensity (or concentration) and quality of a scent using the intensity (amplitude) and pitch (frequency) of a sound to control the output of the odor signal using a sound. Here, the intensity or concentration of a scent represents the degree of strength and weakness of the scent, and the quality of a scent expresses an impression with respect to a specific scent based on the human senses, such as soft, cold, heavy, or the like, which may be expressed by the scent.

The quality of a scent may express a scent such as an aromatic acid scent (citrus), a nutty and sweet scent (vanilla, almond) scent, a cold and fresh scent (herb), a spicy and pungent scent (spicy), a heavy and deep scent (woody), or the like according to scent notes. The present invention may measure the intensity and pitch of a sound at a predetermined time interval on the basis of the above described concept and change the measured intensity and pitch of the sound to a signal for controlling the intensity and quality of an odor.

Figure 4:
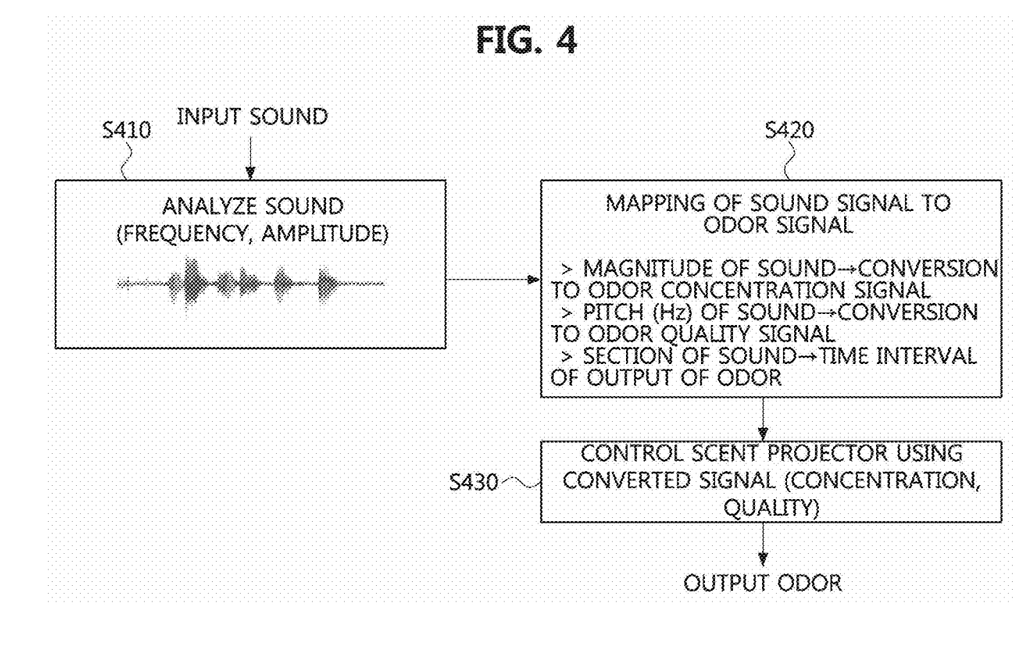
FIG. 4 is a conceptual view showing a method of controlling an output of a scent using a sound according to an example embodiment of the present invention.

FIG. 4 is a conceptual view showing a method of controlling an output of a scent using a sound according to an example embodiment of the present invention.

Referring to FIG. 4, the method of controlling an output of a scent according to the example embodiment of the present invention represents a method of analyzing the frequency and amplitude of an input sound and mapping the analyzed frequency and amplitude to an odor signal.

First, noise is removed from the input sound, and the frequency and amplitude of the sound are analyzed (S410). When the analysis of the frequency and amplitude of the sound is completed, the amplitude of the sound, that is, the magnitude of the sound, is converted into an odor concentration, and the pitch of the sound, which denotes the height of the sound represented by the frequency of the sound, is converted into an odor quality signal (S420).

Here, the analysis of the frequency and amplitude of the sound, and the mapping to the odor signal subsequent to the analysis may be performed, in units of time sections, on discrete signals that are converted from continuous signals in a predetermined time section.

An example embodiment of the method of mapping the amplitude of the sound to the odor concentration may include, when a normally occurring sound has a range of amplitudes of 0 dB to 60 dB, dividing the total range of amplitudes into three equal sections, a section of 0 dB to 20 dB, a section of 21 dB to 40 dB, and a section 41 dB to 60 dB, and applying a different concentration of odor for each section. For example, a section having the smallest amplitude is set to have the minimum jetting intensity of a scent, and a section having the largest amplitude is set to have the maximum jetting intensity of a scent.

Here, a method of determining an amplitude in a time section divided from the entire sound domain may be provided using a method of selecting a maximum value among amplitude values in the time section and a method of calculating and using the average of a plurality of amplitude values present in the time section, or the like.

In addition, an example embodiment of a method of mapping the pitch of a sound to to the odor quality may include dividing a range of human audible frequencies (16 Hz to 20 kHz) into predetermined units of frequency ranges and mapping a different odor quality to each frequency level.

For example, the entire range of audio frequencies may be divided into ten equal sections in 2 kHz increments, and a different odor quality may be mapped to each divided frequency section. Among the divided sections, a low frequency section is mapped to a heavy and deep scent (e.g., a wood scent), and a high frequency section is mapped to a sweet and sour scent.

After completion of the mapping between the sound and the odor as described above, the scent projector is controlled to emit a scent using the converted odor concentration level and the odor quality information (S430).

Figure 5:
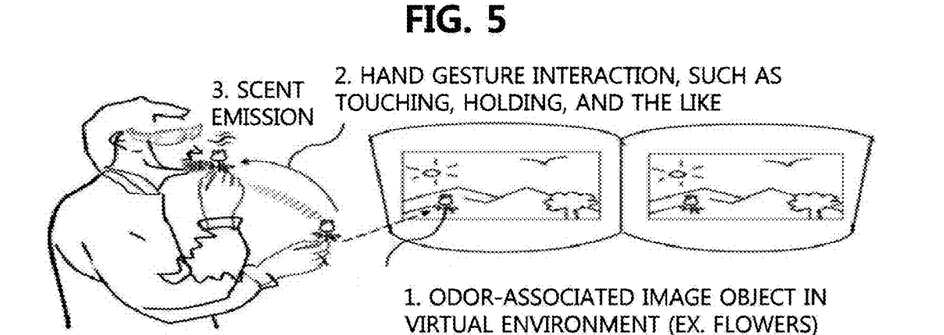
FIG. 5 is a conceptual diagram illustrating scent emission control based on a user interaction according to an example embodiment of the present invention.

A multi-modal virtual augmented reality apparatus according to still another example embodiment of the present invention may perform scent emission control on the basis of a motion of a user to provide the user with an experience of a scent associated with an image object that exists in a screen being output on an image display, That is, the multi-modal virtual augmented reality apparatus according to the present invention may emit a scent associated with an image at a particular point of time during a motion of a user FIG. 5 is a conceptual diagram illustrating scent emission control based on a user interaction according to an example embodiment of the present invention.

Referring to FIG. 5, the virtual augmented reality apparatus according to the example embodiment of the present invention may be controlled to emit a scent whenever a user wearing the virtual augmented reality apparatus naturally moves his or her hand forward in response to a multimedia presented through a display and a speaker of the virtual augmented reality apparatus to touch an object in a virtual space, or holds and moves the object close to his or her nose. In this case, the virtual augmented reality apparatus measures may measure the distance between the user and the object for emitting the scent and adjust the concentration of the odor according to the measured distance.

Figure 6:
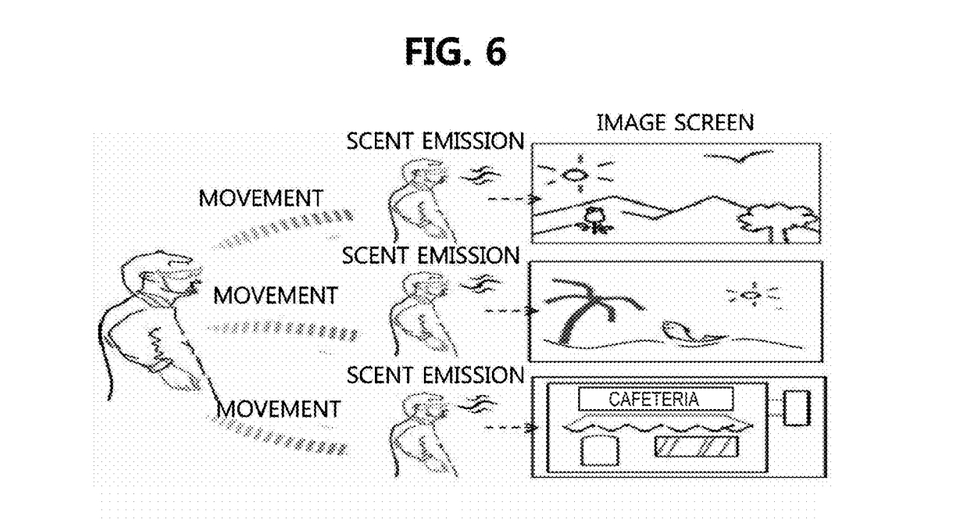
FIG. 6 is a conceptual diagram illustrating scent emission control based on a user interaction according to another example embodiment of the present invention.

FIG. 6 is a conceptual diagram illustrating scent emission control based on a user interaction according to another example embodiment of the present invention.

The virtual augmented reality apparatus according to the example embodiment shown in FIG. 6 may he configured to, when a user moves to a specific environment in a virtual space and enters a specific space, emit a scent suitable for a background of the specific space. The virtual augmented reality apparatus according to the example embodiment shown in FIG. 6 may also measure a distance between the user and the background screen and adjust the concentration of the scent. The virtual spaces according to the example embodiment may be associated with specific odors, for example, a forest, an ocean, a waterfall, a lawn, an arboretum, a flower shop, a restaurant, and the like.

Figure 7:
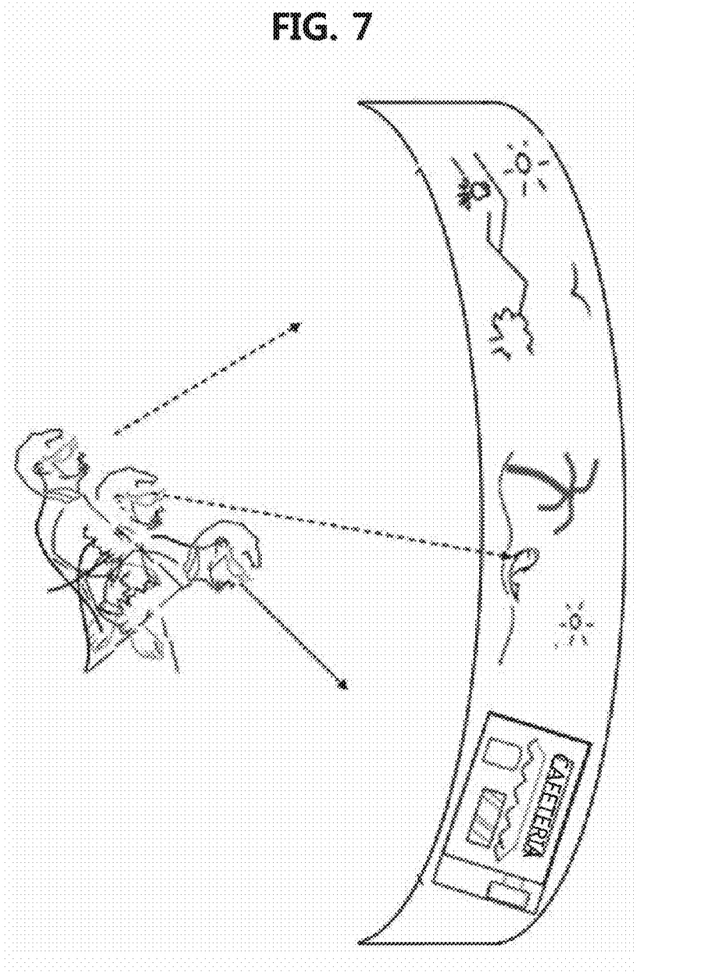
FIG. 7 is a conceptual diagram illustrating scent emission control based on a user interaction according to still another example embodiment of the present invention.

FIG. 7 is a conceptual diagram illustrating scent emission control based on a user interaction according to still another example embodiment of the present invention.

According to the example embodiment shown in FIG. 7, the virtual augmented reality apparatus may be configured to, when a user gazes in a specific direction or gazes at a specific object in a virtual space, control a scent suitable for the specific background or object to be emitted.

Figure 8:
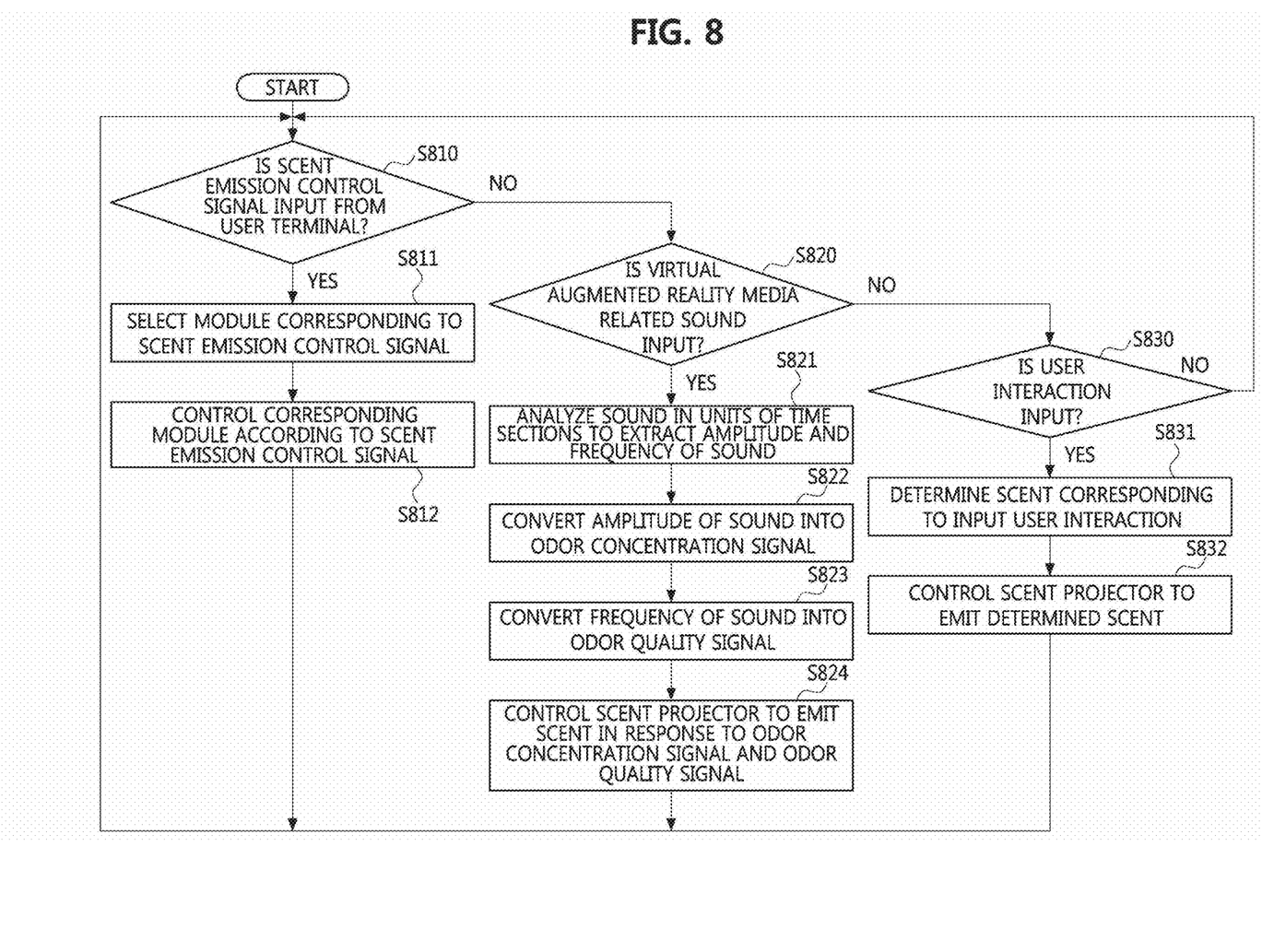
FIG. 8 is an operation flowchart showing a method of providing a virtual augmented reality according to an example embodiment of the present invention.

FIG. 8 is an operation flowchart showing a method of providing a virtual augmented reality according to an example embodiment of the present invention.

The method of providing a virtual augmented reality described through the example embodiment of FIG. 8 may be performed by the virtual augmented reality providing apparatus, the scent projector, or the processor in the virtual augmented reality providing apparatus or the scent projector according to the example embodiment of the present invention. However, an agent of an operation of the method of providing a virtual augmented reality according to the example embodiment of the present invention is not limited thereto. The following description is made on the assumption that the agent of the operation is the virtual augmented reality providing apparatus.

The virtual augmented reality providing apparatus according to the example embodiment of the present invention checks whether a scent emission control signal is input from a user terminal (S810) and selects a module in the scent projector corresponding to the scent emission control signal (S811). The module in the scent projector may include a scent storage, an input valve, an output valve, an air pump, an air tank, an LED lamp, a pressure sensor, and the like.

The virtual augmented reality providing apparatus controls the module in the scent projector according to the scent emission control signal (S812). In this case, the module in the scent projector to be controlled may include at least one module.

Meanwhile, the virtual augmented reality providing apparatus may, when a virtual augmented reality media related sound is input (YES in S820), analyze the sound to extract the amplitude and frequency of the sound at a predetermined time interval (S821).

The virtual augmented reality providing apparatus converts the analyzed amplitude of the sound into an odor concentration signal (S822). Here, the conversion of the amplitude of the sound into the odor concentration signal may include dividing the entire range of amplitudes of the sound into a plurality of sections and setting a different concentration of odor for each of the divided sections.

In addition, the virtual augmented reality providing apparatus converts the analyzed frequency of the sound into an odor quality signal (S823) and controls the scent projector to emit a scent in response to the odor concentration signal and the odor quality signal (S824).

Meanwhile, the virtual augmented reality providing apparatus according to the present invention checks whether a user interaction is input (S830) and determines a scent corresponding to the input user interaction (S831).

When the scent corresponding to the user interaction is determined, the virtual. augmented reality providing apparatus controls the scent projector to emit the determined scent (S832). Here, the user interaction may include at least one of a user's gaze and a to user's motion that are related to an odor associated virtual space and an object in the virtual space.

With the multimodal (an odor, sound, and an image) fusion based virtual augmented reality providing apparatus according to the present invention and the control method thereof, virtual augmented reality information in which an odor, a sound, and an image are fused may be expressed. Accordingly, an effect of a realistic sensation fused with an olfactory sensibility that is not experienced in the existing virtual augmented reality environment may be expected. Accordingly, the virtual augmented reality may be provided as a sensation of experiencing a real environment by responding to a natural motion of a according to the types of user motions or image screens so that the user experiences a new sensory effect in the virtual augmented reality space.

The present invention also provides the headset-shaped virtual augmented reality apparatus, Which generates sensory stimuli of the senses of sight, hearing, and smell, and the scent projector in which an odor is automatically controlled according to the characteristics of a sound.

In addition, according to the present invention, the output of an odor from the scent projector is controlled using air pressure and temperature so that the odor may be rapidly output, and the characteristics of the sound are changed into an odor signal so that a fusion of the sound and the odor may be automatically provided.

In addition, according to the present invention, an interaction of the experiences of the sight, hearing, and smell may be performed on the basis of a motion of the user. In this case, the present invention provides an interactive virtual augmented reality content environment by designating a time point for outputting an odor on the basis of the motion of a user.

As is apparent from the above, the example embodiments of the present invention can suggest a method of providing a new user experience that is not provided by the existing virtual augmented reality apparatus by providing a method of generating an odor in the existing audio/video-based virtual and augmented realities, controlling the intensity and quality of the odor using sound, and allowing an olfactory display to be experienced on the basis of a motion of a user.

The example embodiments of the present invention can increase the sense of reality for a user through simultaneous stimuli of a sound, an image, and an odor while improving the emotional quality of the experience of the user by additionally fusing an odor modality to multimedia (audio/video) provided by the existing virtual and augmented reality apparatuses and providing the odor modality fused multimedia.

The embodiments of the present disclosure may be implemented as program instructions executable by a variety of computers and recorded on a computer readable medium. The computer readable medium may include a program instruction, a data file, a data structure, or a combination thereof. The program instructions recorded on the computer readable medium may be designed and configured specifically for the present disclosure or can be publicly known and available to those who are skilled in the field of computer software.

Examples of the computer readable medium may include a hardware device such as ROM, RAM, and flash memory, which are specifically configured to store and execute the program instructions. Examples of the program instructions include machine codes made by, for example, a compiler, as well as high-level language codes executable by a computer, using an interpreter. The above exemplary hardware device can be configured to operate as at least one software module in order to perform the embodiments of the present disclosure, and vice versa.

While the example embodiments of the present invention and their advantages have been described in detail, it should be understood that various changes, substitutions and alterations may be made herein without departing from the scope of the invention.

What is claimed is:

1. An apparatus for providing a virtual augmented reality using a scent projector, the apparatus comprising:
   a processor; and
   a memory that stores at least one command to be executed by the processor,
   wherein the at least one command includes:
      a command that analyzes an input virtual augmented reality media related sound to extract an amplitude and a frequency of the sound at a predetermined interval of time;
      a command that converts the amplitude of the sound into an odor concentration signal;
      a command that converts the frequency of the sound into an odor quality signal; and
      a command that controls the scent projector to emit a scent in response to the odor concentration signal and the odor quality signal.

2. The apparatus of claim 1, wherein the command that converts the amplitude of the sound into the odor concentration signal includes:
   a command that divides a full amplitude range of the sound into a plurality of sections; and
   a command that sets a concentration of odor for each of the divided sections respectively.

3. The apparatus of claim 2, wherein the command that sets the concentration of odor for each of the divided sections respectively includes a command that sets a low concentration of the odor to a section having a small amplitude among the plurality of sections and sets a high concentration of the odor to a section having a large amplitude among the plurality of sections.

4. The apparatus of claim 1, wherein the command that converts the frequency of the sound into the odor quality signal includes:
   a command that divides an audible frequency range in a frequency range of the sound into a plurality of sections; and
   a command that maps a quality of odor to each of the divided sections respectively.

5. The apparatus of claim 4, wherein the command that maps the quality of the odor to each of the divided sections respectively includes a command that maps a heavy or deep scent to a section including a low frequency band and maps a sweet or aromatic acid scent to a section including a high frequency band.

6. The apparatus of claim 1, wherein the scent projector includes:
   a scent storage including a plurality of scent storage modules, each of which stores a corresponding scent;
   a light emitting diode (LED) lamp configured to heat the scent stored in the scent storage to expedite vaporization of the scent;
   an air pump configured to suction external air and store the suctioned air in an air tank;
   a plurality of input valves connected to the air tank and individual scent storage modules; and
   an output valve connected to the individual scent storage modules to guide scent molecules output from the individual scent storage modules to a corresponding jetting nozzle.

7. The apparatus of claim 6, wherein the scent projector further includes a plurality of jetting nozzles, each set to have a separate inclination angle depending on a position, wherein the scent molecules jetted from the plurality of jetting nozzles are directed to a same position in a space.

8. The apparatus of claim 1, wherein the at least one command further includes a command that receives a scent emission control signal from a user terminal, selects a module in the scent projector corresponding to the control signal, and controls the module in the scent projector in response to the received scent emission control signal.

9. A method of providing a virtual augmented reality using a scent projector, the method comprising:
   analyzing an input virtual augmented reality media related sound to extract an amplitude and a frequency of the sound at a predetermined interval of time;
   converting the amplitude of the sound into an odor concentration signal;

converting the frequency of the sound into an odor quality signal; and controlling the scent projector to emit a scent in response to the odor concentration signal and the odor quality signal.

10. The method of claim 9, wherein the converting of the amplitude of the sound into the odor concentration signal includes:

dividing a full amplitude range of the sound into a plurality of sections; and setting a concentration of odor for each of the divided sections respectively.

11. The method of claim 10, wherein the setting of the concentration of the odor for each of the divided sections respectively includes:

setting a low concentration of the odor to a section having a small amplitude among the plurality of sections; and setting a high concentration of the odor to a section having a large amplitude among the plurality of sections.

12. The method of claim 9, wherein the converting of the frequency of the sound into the odor quality signal includes:

dividing an audible frequency range in a frequency range of the sound into a plurality of sections; and mapping a quality of odor to each of the divided sections respectively.

13. The method of claim 12, wherein the mapping of the quality of the odor to each of the divided sections respectively includes:

mapping a heavy or deep scent to a section including a low frequency band; and mapping a sweet or aromatic acid scent to a section including a high frequency band.

14. The method of claim 9, further comprising:

receiving a scent emission control signal from the user terminal;

selecting a module in the scent projector corresponding to the scent emission control signal; and controlling the module in the scent projector in response to the received scent emission control signal.

15. The method of claim 14, wherein the module in the scent projector includes at least one of a scent storage, an input valve, an output valve, an air pump, an air tank, a light emitting diode (LED) lamp, and a pressure sensor.

16. The method of claim 9, further comprising:

determining a scent corresponding to an input user interaction; and controlling the scent projector to emit the determined scent.

17. The method of claim 16, wherein the user interaction includes at least one of a gaze of a user and a motion of a user that are related to an odor-associated virtual space or object in the virtual space.

* * * * *